(12) United States Patent
Fantini

(10) Patent No.: US 9,068,140 B2
(45) Date of Patent: Jun. 30, 2015

(54) PERFUMING ACETAL

(75) Inventor: Piero Fantini, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/344,054

(22) PCT Filed: Aug. 24, 2012

(86) PCT No.: PCT/EP2012/066533
§ 371 (c)(1),
(2), (4) Date: Mar. 10, 2014

(87) PCT Pub. No.: WO2013/037624
PCT Pub. Date: Mar. 21, 2013

(65) Prior Publication Data
US 2014/0213495 A1  Jul. 31, 2014

(30) Foreign Application Priority Data
Sep. 12, 2011  (EP) ..................... 11180918

(51) Int. Cl.
| | |
|---|---|
| *A61K 8/00* | (2006.01) |
| *C11B 9/00* | (2006.01) |
| *A61K 8/33* | (2006.01) |
| *A61Q 13/00* | (2006.01) |
| *C11D 3/50* | (2006.01) |
| *C11D 3/39* | (2006.01) |
| *C11D 3/395* | (2006.01) |
| *C11D 17/04* | (2006.01) |
| *A61Q 15/00* | (2006.01) |
| *A61Q 5/02* | (2006.01) |
| *A61Q 19/10* | (2006.01) |
| *A61Q 11/00* | (2006.01) |

(52) U.S. Cl.
CPC ............... *C11B 9/0034* (2013.01); *A61K 8/33* (2013.01); *A61Q 13/00* (2013.01); *C11D 3/50* (2013.01); *C11D 3/39* (2013.01); *C11D 3/395* (2013.01); *C11D 17/049* (2013.01); *A61Q 11/00* (2013.01); *A61Q 15/00* (2013.01); *A61Q 5/02* (2013.01); *A61Q 19/10* (2013.01)

(58) Field of Classification Search
CPC ....... C11B 9/0015; C11B 9/0034; A61K 8/33
USPC .......................................... 512/23
See application file for complete search history.

(56) References Cited

U.S. PATENT DOCUMENTS 6,277,796 B1    8/2001  Sivik et al.
2012/0010114 A1  1/2012  Dupau et al.

FOREIGN PATENT DOCUMENTS

FR           1376861 A    10/1964
WO       2010/122451 A1   10/2010
WO    WO 2010/122451 A1   10/2010

OTHER PUBLICATIONS

I. N. Nazarov et al., Zhurnal Obshchei Khimii vol. 30, pp. 2269-2274, 1960 (abstract).*
E. Wenkert et al., Journal of the American Chemical Society vol. 100, pp. 1267-1273, 1978 (abstract).*
Blakeway et al., "Chemical reactions in perfume ageing," International Journal of Cosmetic Science, 9:203-214 (1987).
International Search Report and Written Opinion, Application No. PCT/EP2012/066533, Nov. 23, 2012.

* cited by examiner

*Primary Examiner* — John Hardee
(74) *Attorney, Agent, or Firm* — Winstron & Strawn LLP

(57) ABSTRACT

The present invention concerns the use as perfuming ingredient of 4-dimethoxymethyl-1,3-dimethyl-1-cyclohexene in the form of any one of its stereoisomers or a mixture thereof, for instance to impart odor notes of the grapefruit and floral type.

7 Claims, No Drawings

PERFUMING ACETAL

TECHNICAL FIELD

The present invention relates to the field of perfumery. More particularly, it concerns the use as perfuming ingredient of 4-dimethoxymethyl-1,3-dimethyl-1-cyclohexene. Furthermore, following what is mentioned herein, the present invention comprises the invention's compound as part of a perfuming composition or of a perfuming consumer product.

PRIOR ART

The compound of formula (I) is known as such in the literature, e.g. it is mentioned in the US TSCA Chemical Substance Inventory without any mention of its use. However, said document does not report or suggest any organoleptic properties of the compound of formula (I), or any use of said compound in the field of perfumery.

To the best of our knowledge, the closest analogue reported in the context of perfumery is 4-diethoxymethyl-1,3-dimethyl-1-cyclohexene which is mentioned (in *Inter. J. of Cosmetic. Sci.* 1987, 9, 203) as being a degradation product of some perfumes containing the triplal aldehyde (2,4-dimethyl-cyclohex-3-enecarbaldehyde) and ethanol. No odor description is provided for this compound but, as a person skilled in the art knows, the fact of being observed as an ageing by-product is certainly not a motivation or a suggestion to use analogues in the art of perfumery. Said prior art document does not report or suggest any organoleptic properties of the compounds of formula (I), or any use of said compounds in the field of perfumery.

DESCRIPTION OF THE INVENTION

We have now surprisingly discovered that a compound of formula

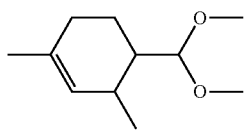

(I)

in the form of any one of its stereoisomers or a mixture thereof;
can be used as perfuming ingredient, for instance to impart odor notes of the grapefruit and floral type.

For the sake of clarity, by the expression "any one of its stereoisomers", or the similar, it is meant the normal meaning understood by a person skilled in the art, i.e. that the invention's compound can be a pure enantiomer (if chiral) or diastereomer (e.g. the ring substituents are in a conformation cis or trans).

As specific examples of the invention's compounds, one may cite, as non-limiting example, cis-4-dimethoxymethyl-1,3-dimethyl-1-cyclohexene which is characterized by a sweet citrus note of the pink grapefruit type which is associated with a floral/peony note. The citrus note of the present compound is of particular interest, since it reminds strongly of the natural juicy pink grapefruit odor, but without the pungent sulfur note typical of the generic grapefruit note commercially available. The natural grapefruity, juicy/sweet note, as well as the peony aspect, characteristic of this invention's compound renders the latter particularly suitable for imparting a nice, juicy, cosmetic grapefruity aspect to the perfuming composition where it is added.

According to a particular embodiment of the invention, the use of said compound is even more remarkable when admixed with other grapefruit odorants, such as 8-mercapto-3-p-menthanone, cis-2-methyl-4-propyl-1,3-oxathiane, 6,6-dimethoxy-2,5,5-trimethyl-2-hexene, 1-p-menthene-8-thiol.

The isomer trans-4-dimethoxymethyl-1,3-dimethyl-1-cyclohexene possesses an odor similar to the one of the cis, but distinguishes itself by having a terpenic aspect.

According to a particular embodiment of the invention, said invention's compound is in the form of a mixture of cis and trans stereoisomers comprising between about 70% and about 100% of the cis stereoisomer and between about 30% and about 0% of the trans stereoisomer.

According to a particular embodiment of the invention, said invention's compound is cis-4-dimethoxymethyl-1,3-dimethyl-1-cyclohexene.

Table 1 herein below reports the odor of the invention's compounds compared with that of the corresponding diethyl acetals.

TABLE 1

Odor properties of the dimethyl and di ethyl acetals

| Compound structure and name | Odor notes |
|---|---|
| cis-4-dimethoxymethyl-1,3-dimethyl-1-cyclohexene | Sweet citrus/pink grapefruit note with floral/peony note. Reminds strongly of the natural juicy pink grapefruit odor |
| trans-4-dimethoxymethyl-1,3-dimethyl-1-cyclohexene | Odor similar to the cis isomer having also a terpenic aspect |
| Comparative examples | |
| cis-4-diethoxymethyl-1,3-dimethyl-1-cyclohexene | Green, minty, acidic, fruity odor. Far less powerful, natural and fresh than the invention's compound |
| trans-4-diethoxymethyl-1,3-dimethyl-1-cyclohexene | Much weaker than the cis isomer, and more minty |

When the odor of the invention's compounds is compared with that of the prior art diethyl acetals, for which no odor disclosure is provided in the prior art, then the invention's compounds distinguish themselves by the association of sweet citrus and floral note, a clearly stronger and natural odor, as well as by lacking the minty, acidic notes so characteristic of the prior art compounds. Said differences lend the invention's compounds to be hedonically suitable for a use in the perfumery industry to the contrary of the prior art diethyl acetals.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modem perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 30% by weight, or even more, of the compounds of the invention based on the weight of the composition into which they are incorporated. Concentrations lower than these, such as in the order of 0.001% to 15% by weight, can be used when these compounds are incorporated into perfumed articles, percentage being relative to the weight of the article.

The invention's compounds can be prepared according to a method as described in the Examples, e.g. by acetalisation of the corresponding aldehyde.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

Preparation of the stereoisomers of 4-dimethoxymethyl-1,3-dimethyl-1-cyclohexene Cis-4-dimethoxymethyl-1,3-dimethyl-1-cyclohexene Amberlyst A15 (1.46 g) was placed into a 1-liter, 4-necked round bottom flask. Anhydrous methanol (32.40 g, 1.00 mole) was added, followed by the 2,4-dimethyl-3-cyclohexen-1-carboxaldehyde (140.00 g, 1.00 mole, in the form of a 84/16 mixture of cis/trans isomers). The mixture was stirred at room temperature, and triethyl ortho formate (118.00 g, 1.10 mole) was introduced over 1 hour. An exothermal reaction occurred, the temperature rose from 23° C. to 34° C. The reaction was allowed to cool to RT over 1.5 hours. The Amberlyst A15 was filtered off, and the solvent removed under vacuum (40° C./10 mbar). The crude product (184.00 g, 98.2% pure by GC; 97.7% Crude Yield) was then distilled through a 15 cm Vigreux column. Pooling of the pure fractions afforded the desired acetal (175.39 g, yield=94.8%, mixture of 14.8% trans/85.2% cis isomers).

Bp=85° C./9.3 mbar.

$^{13}C$ NMR: 15.4 (q); 19.3 (t); 23.5 (q); 29.8 (d); 30.5 (t); 38.6 (d); 52.4 (q); 52.6 (q); 105.6 (d); 127.5 (d); 132.9 (s).

Trans-4-dimethoxymethyl-1,3-dimethyl-1-cyclohexene

1) The 2,4-dimethyl-3-cyclohexen-1-carboxaldehyde (188.75 g, 1.37 mole, 84/16 cis/trans) was dissolved in anhydrous methanol (200.2 g) at room temperature. Solid sodium methoxide (7.45 g, 0.138 mole) was added portionwise. The reaction temperature rose from 23° C. to 39° C. The mixture was heated to reflux (65° C.) for 2 hours, to obtain a stable isomer ratio (81.1% trans/18.9% cis). After cooling to RT, glacial acetic acid (8.33 g, 0.139 mole) was added dropwise. The methanol was removed under vacuum, and the residue diluted with tert-butyl methyl ether (300 ml), and washed with water (100 ml), 10% aq. $K_2CO_3$ (50 ml), and water (50 ml). The organic phase was dried over $Na_2SO_4$, filtered and the solvent removed in vacuuo. The crude product (198.27 g) was distilled through a 15 cm Vigreux column, to afford the desired epimerized mixture (168.5 g, 89.5% Yield, 81.1% trans/18.9% cis)

$^{13}C$ NMR: 20.6 (q); 22.0 (t); 23.4 (q); 28.4 (t); 29.9 (d); 53.5 (d); 125.8 (d); 133.2 (s); 205.0 (d).

2) 0.23 g Amberlyst A15, 3.37 g (105 mmole), anhydrous methanol, 13.86 g (100 mmole) trans-2,4-dimethyl-3-cyclohexen-1-carboxaldehyde trimethyl ortho formate (12.76 g, 120 mole) were added over 2.5 hours. Evaporation of the volatiles afforded the crude product (18.38 g, 100% pure by GC, 99.5% yield). Distillation through a 10 cm Vigreux column afforded the desired acetal (14.68 g, 79.4% yield, as a mixture 80.5/19.5 trans/cis isomers).

$^{13}C$ NMR: 20.5 (t); 21.3 (q); 23.6 (q); 28.2 (t); 30.7 (d); 41.9 (d); 53.9 (q); 54.3 (q); 106.1 (d); 126.7 (d); 132.9 (s).

Comparative Example 1

Cis-4-diethoxymethyl-1,3-dimethyl-1-cyclohexene

Amberlyst A 15 (1.42 g), anhydrous ethanol (47.07 g, 1.02 mole) and aldehyde (174.06 g, 1.26 mole) were stirred at room temperature. Triethyl orthoformate (162.78 g, 1.10 mole) was added dropwise over 1.25 hours. The reaction temperature rose from 23° C. to 47° C. After 1 hour, the mixture was then heated to 50° C. and a fresh portion of triethyl orthoformate (30.11 g, 0.20 mole) was added over 30 minutes.

Filtration of the Amberlyst, and evaporation of the volatiles under vacuum afforded the crude diethyl acetal (252.06 g, 85.4% pure).

Fractional distillation through a 15 cm Vigreux column afforded the desired product (175.05 g, 65.6% yield, mixture of 25.4% trans and 74.6% cis isomers).

$^{13}$C NMR: 15.4 (q); 15.4 (q); 19.4 (t); 23.5 (q); 29.9 (d); 30.5 (t); 39.4 (d); 60.5 (t); 60.9 (t); 104.2 (d); 127.6 (d); 132.8 (s).

Trans-4-diethoxymethyl-1,3-dimethyl-1-cyclohexene

Amberlyst A15 (0.27 g), anhydrous ethanol (4.67 g, 101 mmole), and the aldehyde (13.83 g, 121 mmole, mixture of 81.2% trans/18.8% cis isomers) were stirred at room temperature. Triethyl orthoformate (17.87 g, 121 mmole) was added dropwise over 2 hours. Filtration of the Amberlyst and evaporation of the volatiles under vacuum afforded the crude diethyl acetal (20.44 g, 98.2% pure).

Fractional distillation through a 15 cm Vigreux column afforded the desired product (18.43 g, 86.7% yield, mixture of 80.9% trans/19.1% cis isomers).

$^{13}$C NMR: 15.4 (q); 20.7 (t); 21.3 (q); 23.6 (q); 28.3 (t); 30.8 (d); 42.8 (d); 62.3 (t); 62.4 (t); 104.2 (d); 126.9 (d); 132.9 (s).

Example 2

Preparation of a Perfuming Composition

A perfuming composition for shower gel, of the citrus/grapefruit type, was prepared by admixing the following ingredients:

| Parts by weight | Ingredient |
| --- | --- |
| 40 | Benzyl acetate |
| 60 | 10%* Cis-3-hexenol acetate |
| 50 | 10%* Acetophenone |
| 10 | Aldehyde C 10 |
| 50 | 10%* Aldehyde C 12 |
| 10 | Aldehyde C 8 |
| 20 | 10%* Gamma nonalactone |
| 20 | 10%* Ethyl butyrate |
| 30 | 10%* Carvone Gauche |
| 10 | Citral |
| 50 | 10%* Cis-3-hexenol |
| 100 | Coranol [1] |
| 10 | Allyl 3-cyclohexylpropanoate |
| 10 | Gamma Decalactone |
| 30 | 10%* Dorinone ® [2] Beta |
| 20 | Allyl heptanoate |
| 20 | Phenylethyl isobutyrate |
| 150 | Limette |
| 800 | Limonene |
| 380 | Linalool |
| 100 | Tangerine essential oil |
| 20 | Myrrhone ® [3] |
| 100 | Hedione ® [4] |
| 50 | 1%* (1R,4R)-8-mercapto-3-p-menthanone |
| 40 | Beta Ionone |
| 20 | 2,4-dimethyl-3-cyclohexen-1-carboxaldehyde |
| 2200 | |

*in dipropyleneglycol
[1] 4-cyclohexyl-2-methyl-2-butanol; origin: Firmenich SA, Geneva, Switzerland
[2] 1-(2,6,6-trimethyl-1-cyclohexen-1-yl)-2-buten-1-one; origin: Firmenich SA, Geneva, Switzerland
[3] 4-(2,2,C-3,T-6-tetramethyl-R-1-cyclohexyl)-3-buten-2-one; origin: Firmenich SA, Geneva, Switzerland
[4] methyl dihydrojasmonate; origin: Firmenich SA, Geneva, Switzerland The addition of 800 parts by weight of cis-4-dimethoxymethyl-1,3-dimethyl-1-cyclohexene to the above-described composition imparted to the latter a remarkably juicy pink grapefruit connotation, transforming the original fragrance from a lime character to a grapefruit character.

The addition of the same amount of the cis-4-diethoxymethyl-1,3-dimethyl-1-cyclohexene imparted to the above-described composition an unpleasant effect characterized by a fruity, acidic minty note, which twisted the original fragrance toward a poorly natural/elegant acidic note.

Example 3

Preparation of a Perfuming Composition

A perfuming composition for a man's Eau de Toilette, of the woody-floral type, was prepared by admixing the following ingredients:

| Parts by weight | Ingredient |
| --- | --- |
| 120 | Linalyl acetate |
| 10 | Styrallyl acetate |
| 10 | 10%* Aldehyde C 12 |
| 70 | Hexylcinnamic aldehyde |
| 60 | 10%* Ambrox ® [1] Super |
| 50 | 50%* Benjoin oil |
| 130 | Bergamot essential oil |
| 40 | Atlas Cedar oil |
| 130 | Cedar oil |
| 60 | Cedrol |
| 70 | Lemon essential oil |
| 70 | Citronellol |
| 80 | Coranol [2] |
| 20 | Elemi essential oil |
| 50 | Exaltolide ® [3] Total |
| 50 | Florol ® [4] |
| 10 | Geranium essential oil |
| 80 | Hydroxycitronellal |
| 2000 | Iso E ® [5] Super |
| 40 | Lilial ® [6] |
| 70 | Magnolan ® [7] |
| 20 | Crystal moss |
| 400 | Hedione ® [8] |
| 140 | Patchouli essential oil |

-continued

| Parts by weight | Ingredient |
|---|---|
| 50 | Pepper essential oil |
| 20 | Orange essential oil |
| 10 | Rhubofix ® [9)] |
| 40 | Rose Centifolia oil |
| 100 | Vetyver essential oil |
| 4000 | |

*in dipropyleneglycol
[1)] (-)-(8R)-8,12-epoxy-13,14,15,16-tetranorlabdane; origin: Firmenich SA, Geneva, Switzerland
[2)] 4-cyclohexyl-2-methyl-2-butanol; origin: Firmenich SA, Geneva, Switzerland
[3)] pentadecanolide; origin: Firmenich SA, Geneva, Switzerland
[4)] tetrahydro-2-isobutyl-4-methyl-4(2H)-pyranol; origin: Firmenich SA, Geneva, Switzerland
[5)] 1-(octahydro-2,3,8,8-tetramethyl-2-naphthalenyl)-1-ethanone; origin: Firmenich SA, Geneva, Switzerland
[6)] 3-(4-tert-butylphenyl)-2-methylpropanal; origin: Givaudan SA, Vernier, Switzerland
[7)] 2,4-dimethyl-4,4a,9,9a-tetrahydroindeno[2,1-d][1,3]dioxin; origin: Symrise, Germany
[8)] methyl dihydrojasmonate; origin: Firmenich SA, Geneva, Switzerland
[9)] 3',4-dimethyl-tricyclo[6.2.1.0(2,7)]undec-4-ene-9-spiro-2'-oxirane; origin: Firmenich SA, Geneva, Switzerland The addition of 300 parts by weight of cis-4-dimethoxymethyl-1,3-dimethyl-1-cyclohexene to the above-described composition imparted to the above Eau de toilette a clear and very nice and juicy citrus connotation evoking the grapefruit.

The addition of the same amount of the cis-4-diethoxymethyl-1,3-dimethyl-1-cyclohexene imparted to the above-described a faint effect characterized by a fruity, acidic note, which twisted the original fragrance toward a poorly natural/elegant odor.

What is claimed is:

1. A method to confer, enhance, improve or modify the odor properties of a perfuming composition or of a perfumed article, which method comprises adding to said composition or article an effective amount of at least a compound of formula

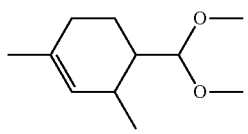

(I)

in the form of any one of its stereoisomers or a mixture thereof.

2. A method according to claim 1, wherein said invention's compound is in the form of a mixture of cis and trans stereoisomers comprising between about 70% and about 100% of the cis stereoisomer and between about 30% and about 0% of the trans stereoisomer.

3. A method Use according to claim 1 or 2, wherein said compound is cis-4-dimethoxymethyl-1,3-dimethyl-1-cyclohexene.

4. A perfuming composition comprising
   i) at least one compound of formula

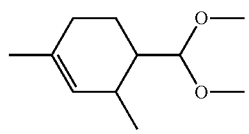

(I)

in the form of any one of its stereoisomers or a mixture thereof;
   ii) at least one ingredient selected from the group consisting of a perfumery carrier and a perfumery base; and
   iii) optionally at least one perfumery adjuvant.

5. A perfuming consumer product comprising:
   i) at least one compound of formula

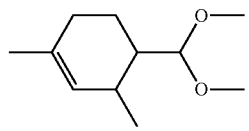

(I)

in the form of any one of its stereoisomers or a mixture thereof; and
   ii) a perfumery consumer base.

6. A perfuming consumer product according to claim 5, wherein the perfumery consumer base is a perfume, a fabric care product, a body-care product, an air care product or a home care product.

7. A perfuming consumer product according to claim 5, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *

UNITED STATES PATENT AND TRADEMARK OFFICE
CERTIFICATE OF CORRECTION

PATENT NO.        : 9,068,140 B2                                      Page 1 of 1
APPLICATION NO.   : 14/344054
DATED             : June 30, 2015
INVENTOR(S)       : Fantini It is certified that error appears in the above-identified patent and that said Letters Patent is hereby corrected as shown below:

In the claims

Column 10:
Line 4 (claim 3, line 1), after "A method", delete "Use".

Signed and Sealed this
Twentieth Day of October, 2015

Michelle K. Lee
*Director of the United States Patent and Trademark Office*